United States Patent [19]

Dürr

[11] Patent Number: 5,217,521
[45] Date of Patent: Jun. 8, 1993

[54] TRIAZOLYLSULFONAMIDES

[75] Inventor: Dieter Dürr, Bottmingen, Switzerland

[73] Assignee: Ciba-Geigy Corporation, Ardsley, N.Y.

[21] Appl. No.: 884,260

[22] Filed: May 8, 1992

Related U.S. Application Data

[63] Continuation of Ser. No. 628,775, Dec. 17, 1990.

[30] Foreign Application Priority Data

Dec. 22, 1989 [CH] Switzerland .................. 4643/89
Aug. 14, 1990 [CH] Switzerland .................. 2638/90

[51] Int. Cl.$^5$ .................................................. A01N 43/50
[52] U.S. Cl. .................................... 504/241; 544/263; 548/263.8; 504/178; 504/185
[58] Field of Search .......................... 71/92; 544/263

[56] References Cited

U.S. PATENT DOCUMENTS

| | | | |
|---|---|---|---|
| 2,444,606 | 7/1948 | Heimbach et al. | 544/263 |
| 4,734,123 | 3/1988 | Monte | 544/263 |
| 4,854,964 | 8/1989 | Jelich et al. | 71/92 |
| 4,954,163 | 9/1990 | Kleschik et al. | 544/263 |
| 4,981,507 | 1/1991 | Jelich | 544/263 |
| 4,988,812 | 1/1991 | Kim et al. | 544/263 |
| 5,041,157 | 8/1991 | Seiler et al. | 544/263 |
| 5,071,468 | 10/1991 | Astles | 71/92 |
| 5,175,289 | 12/1992 | Seiler | 544/263 |

FOREIGN PATENT DOCUMENTS

| | | | |
|---|---|---|---|
| 0142152 | 5/1985 | European Pat. Off. | |
| 0256396 | 2/1988 | European Pat. Off. | |
| 0337947 | 10/1989 | European Pat. Off. | 544/263 |
| 0343752 | 11/1989 | European Pat. Off. | |
| 0375076 | 6/1990 | European Pat. Off. | |
| 0378508 | 7/1990 | European Pat. Off. | 544/263 |
| 0070311 | 7/1969 | German Democratic Rep. | |
| 8910368 | 11/1989 | World Int. Prop. O. | |

Primary Examiner—Donald G. Daus
Attorney, Agent, or Firm—Kevin T. Mansfield; Edward McC. Roberts

[57] ABSTRACT

N-Phenyl-triazolopyrimidinyl-sulfonamides of formula I

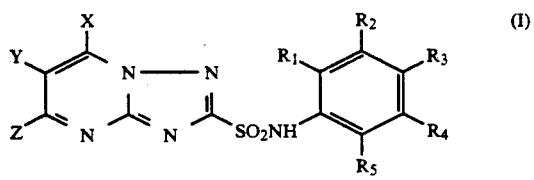

wherein
$R_1$ is halogen, phenyl, O-phenyl, $C_1$-$C_4$alkyl, $C_1$-$C_4$haloalkyl, —$OR_8$, —$OR_9$, nitro, hydroxy, cyano, —$SR_6$, —$SOR_6$, —$SO_2R_6$, —$SR_8$, —$SOR_8$, —$SO_2R_8$, —$SO_3R_8$, —$SR_9$, —$SOR_9$, —$SO_2R_9$, —$SO_2NR_{10}(R_{10})$, —$SO_3R_9$, —$COOR_7$, —$CONHR_9$, —$CONR_9(R_9)$, formyl,

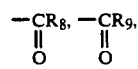

—$NH_2$, —$NHR_9$ or —$NR_9(R_9)$;
$R_2$ and $R_4$ independently of one another are hydrogen, halogen, $C_1$-$C_4$alkyl, —$COOR_7$ or —$OR_9$;
$R_3$ is hydrogen or halogen;
$R_5$ is hydrogen, halogen, phenyl, O-phenyl, $C_1$-$C_4$alkyl, $C_1$-$C_4$haloalkyl, —$OR_8$, —$OR_9$, nitro, hydroxy, cyano, —$SR_6$, —$SOR_6$, —$SO_2R_6$, —$SR_8$, —$SOR_8$, —$SO_3R_8$, —$SR_9$, —$SOR_9$, —$SO_2R_9$, —$SO_2NR_{10}(R_{10})$, —$SO_3R_9$, —$COOR_7$, —$CONHR_9$, —$CONR_9(R_9)$, formyl,

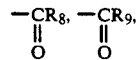

—$NH_2$, —$NHR_9$ or —$NR_9(R_9)$;
$R_6$ is hydrogen, phenyl, benzyl, $C_2$-$C_4$alkenyl, $C_2$-$C_4$alkynyl, or $C_1$-$C_4$alkyl substituted by —$OR_9$;
$R_7$ is $C_1$-$C_4$alkyl, $C_2$-$C_4$alkenyl, $C_2$-$C_4$alkynyl, phenyl or benzyl;
$R_8$ is $C_1$-$C_4$haloalkyl;
$R_9$ is $C_1$-$C_4$alkyl;
$R_{10}$ is hydrogen or $C_1$-$C_4$alkyl;
X, Y and Z independently of one another are hydrogen, $C_1$-$C_4$alkyl, $C_1$-$C_4$haloalkyl, phenylthio, benzylthio, hydroxy, halogen, —$OR_8$, —$OR_9$, $C_1$-$C_4$alkyl substituted by —$OR_9$, $C_1$-$C_4$alkyl substituted by —$OR_8$, or —$NH_2$, —$NHR_9$, —$NR_9(R_9)$, $C_3$-$C_6$cycloalkyl, $C_3$-$C_6$cycloalkyl substituted by halogen, —$OR_8$, —$OR_9$, —$SR_8$, —$SR_9$ or by $C_1$-$C_4$alkyl, or X and Y together or Y and Z together form a $C_2$-$C_3$alkylene bridge which may be interrupted by oxygen or sulfur;

with the proviso that at least one of the substituents X, Y and Z is $C_3$-$C_6$cycloalkyl or $C_3$-$C_6$cycloalkyl substituted by halogen, —$OR_8$, —$OR_9$, —$SR_8$, —$SR_9$ or by $C_1$-$C_4$alkyl, and the salts of those compounds, have good pre- and postemergent selective herbicidal and growth regulating properties.

20 Claims, No Drawings

TRIAZOLYLSULFONAMIDES

This application is a continuation, of application Ser. No. 628,775, filed Dec. 17, 1990.

The present invention relates to novel herbicidally active and plant growth regulating N-phenyl-triazolopyrimidinylsulfonamides, to processes for their preparation, to compositions containing them as active ingredients, and to their use for controlling weeds, especially selectively in crops of useful plants, or for regulating and inhibiting plant growth.

Triazolylsulfonamides having herbicidal activity are known from European Patent Application No. 0 142 152. However, the compounds disclosed therein are not always able to satisfy requirements as regards potency, selectivity and persistence. There is therefore a need for compounds having better activity and greater selectivity.

Novel triazolylsulfonamides having improved herbicidal and plant growth regulating activity have now been found.

The N-phenyl-triazolopyrimidinylsulfonamides according to the invention have the formula I $$\text{(I)}$$

wherein $R_1$ is halogen, phenyl, O-phenyl, $C_1$-$C_4$alkyl, $C_1$-$C_4$haloalkyl, —$OR_8$, —$OR_9$, nitro, hydroxy, cyano, —$SR_6$, —$SOR_6$, —$SO_2R_6$, —$SR_8$, —$SOR_8$, —$SO_2R_8$, —$SO_3R_8$, —$SR_9$, —$SOR_9$, —$SO_2R_9$, —$SO_2NR_{10}(R_{10})$, —$SO_3R_9$, —$COOR_7$, —$CONHR_9$, —$CONR_9(R_9)$, formyl, $$-CR_8, \quad -CR_9,$$
$$\|\quad\quad\quad\|$$
$$O\quad\quad\quad O$$

—$NH_2$, —$NHR_9$ or —$NR_9(R_9)$;

$R_2$ and $R_4$ independently of one another are hydrogen, halogen, $C_1$-$C_4$alkyl, —$COOR_7$ or —$OR_9$;

$R_3$ is hydrogen or halogen;

$R_5$ is hydrogen, halogen, phenyl, O-phenyl, $C_1$-$C_4$alkyl, $C_1$-$C_4$haloalkyl, —$OR_8$, —$OR_9$, nitro, hydroxy, cyano, —$SR_6$, —$SOR_6$, —$SO_2R_6$, —$SR_8$, —$SOR_8$, —$SO_3R_8$, —$SR_9$, —$SOR_9$, —$SO_2R_9$, —$SO_2NR_{10}(R_{10})$, —$SO_3R_9$, —$COOR_7$, —$CONHR_9$, —$CONR_9(R_9)$, formyl, $$-CR_8, \quad -CR_9,$$
$$\|\quad\quad\quad\|$$
$$O\quad\quad\quad O$$

—$NH_2$, —$NHR_9$ or —$NR_9(R_9)$;

$R_6$ is hydrogen, phenyl, benzyl, $C_2$-$C_4$alkenyl, $C_2$-$C_4$alkynyl, or $C_1$-$C_4$alkyl substituted by —$OR_9$;

$R_7$ is $C_1$-$C_4$alkyl, $C_2$-$C_4$alkenyl, $C_2$-$C_4$alkynyl, phenyl or benzyl;

$R_8$ is $C_1$-$C_4$haloalkyl;

$R_9$ is $C_1$-$C_4$alkyl;

$R_{10}$ is hydrogen or $C_1$-$C_4$alkyl;

X, Y and Z independently of one another are hydrogen, $C_1$-$C_4$alkyl, $C_1$-$C_4$haloalkyl, phenylthio, benzylthio, hydroxy, halogen, —$OR_8$, —$OR_9$, $C_1$-$C_4$alkyl substituted by —$OR_9$, $C_1$-$C_4$alkyl substituted by —$OR_8$, or —$NH_2$, —$NHR_9$, —$NR_9(R_9)$, $C_3$-$C_6$cycloalkyl, $C_3$-$C_6$cycloalkyl substituted by halogen, —$OR_8$, —$OR_9$, —$SR_8$, —$SR_9$ or by $C_1$-$C_4$alkyl, or X and Y together or Y and Z together form a $C_2$-$C_3$alkylene bridge which may be interrupted by oxygen or sulfur;

with the proviso that at least one of the substituents X, Y and Z is $C_3$-$C_6$cycloalkyl or $C_3$-$C_6$cycloalkyl substituted by halogen, —$OR_8$, —$OR_9$, —$SR_8$, —$SR_9$ or by $C_1$-$C_4$alkyl, and the salts of those compounds.

In the definitions of the substituents, $C_1$-$C_4$alkyl is to be understood as being straight-chained or branched alkyl, for example methyl, ethyl, n-propyl, isopropyl, n-butyl, sec.-butyl, isobutyl and tert.-butyl. The alkyl groups present as substituents or in the substituents preferably have 1 or 2 carbon atoms. Methyl is especially preferred.

The $C_2$-$C_4$alkenyl radicals in the substituents $R_6$ and $R_7$ may be straight-chained or branched. Alkenyl radicals having a chain length of two or three carbon atoms are preferred. Examples of $C_2$-$C_4$alkenyl radicals are: vinyl, allyl, methallyl, 1-methylvinyl, but-2-en-1-yl. Vinyl and allyl are preferred.

The $C_2$-$C_4$alkynyl radicals in the definitions of the substituents $R_6$ and $R_7$ may be straight-chained or branched. Alkynyl radicals having a chain length of 2 or 3 carbon atoms are preferred. $C_2$-$C_4$alkynyl radicals are, for example, ethynyl, propargyl, 1-propynyl, 3-butynyl or 1-methylpropargyl, ethynyl and propargyl being especially preferred.

Halogen by itself and as part of a substituent such as haloalkyl is to be understood as being fluorine, chlorine and bromine, but preferably fluorine and chlorine. Haloalkyl is generally chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl, 1,1,2,3,3,3-hexafluoropropyl, but especially fluoromethyl, chloromethyl, difluoromethyl and trifluoromethyl.

The $C_3$-$C_6$cycloalkyl groups in the definitions of the substituents X, Y and Z may be substituted or unsubstituted and include, for example, cyclopropyl, 2-fluorocyclopropyl, 2,4-difluorocyclopropyl, 2-chlorocyclopropyl, 2,3-dichlorocyclopropyl, 2-methylcyclopropyl, 2-methylthiocyclopropyl, 2,3-dimethylcyclopropyl, 2-methoxycyclopropyl, cyclobutyl, cyclopentyl, 3-methylcyclopentyl, 3,4-dimethoxycyclopentyl, cyclohexyl, 3-fluorocyclohexyl, 4-methylcyclohexyl and 4-methylthiocyclohexyl.

The invention relates also to the salts that the compounds of formula I are able to form with amines, alkali metal bases and alkaline earth metal bases.

Of the alkali metal and alkaline earth metal hydroxides that are suitable as salt formers, special mention should be made of the hydroxides of lithium, sodium, potassium, magnesium and calcium, but especially those of sodium and potassium.

Examples of amines suitable for salt formation are primary, secondary and tertiary aliphatic and aromatic amines, such as methylamine, ethylamine, propylamine, isopropylamine, the four isomers of butylamine, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, but especially ethyl-, propyl-, diethyl- and triethyl-amine, and more especially isopropylamine and diethanolamine.

Of the compounds of formula I, preference is given to those wherein $R_1$ is halogen, nitro, $C_1$-$C_4$-alkyl, $C_1$-$C_4$-haloalkyl, —$OR_8$, —$OR_9$, hydroxy, cyano or —$COOR_7$;

$R_5$ is hydrogen, halogen, nitro, $C_1$-$C_4$alkyl, $C_1$-$C_4$-haloalkyl, —$OR_8$, —$OR_9$, hydroxy, cyano or —$COOR_7$; and X, Y and Z independently of one another are hydrogen, $C_1$-$C_4$alkyl, $C_1$-$C_4$haloalkyl, $C_1$-$C_4$alkyl substituted by —$OR_9$, $C_1$-$C_4$alkyl substituted by —$OR_8$, or halogen, $C_3$-$C_6$cycloalkyl or $C_3$-$C_6$cycloalkyl substituted by halogen, —$OR_8$, —$OR_9$, —$SR_8$, —$SR_9$ or by $C_1$-$C_4$alkyl.

In an especially preferred group of compounds of formula I, $R_1$ is halogen, nitro, $C_1$-$C_2$alkyl, $C_1$-$C_2$haloalkyl, —$OR_8$, —$OR_9$, hydroxy, cyano or —$COOR_7$;

$R_2$ and $R_4$ independently of one another are hydrogen, halogen, $C_1$-$C_2$alkyl, —$COOR_7$ or —$OR_9$;

$R_5$ is hydrogen, halogen, nitro, $C_1$-$C_2$alkyl, $C_1$-$C_2$haloalkyl, —$OR_8$, —$OR_9$, hydroxy, cyano or —$COOR_7$;

$R_7$ is $C_1$-$C_2$alkyl, $C_2$-$C_3$alkenyl, $C_2$-$C_3$alkynyl, phenyl or benzyl; $R_8$ is $C_1$-$C_2$haloalkyl; $R_9$ is $C_1$-$C_2$alkyl; and X, Y and Z independently of one another are hydrogen, $C_1$-$C_2$alkyl, $C_1$-$C_2$haloalkyl, halogen, $C_1$-$C_4$alkyl substituted by —$OR_9$, $C_1$-$C_4$alkyl substituted by —$OR_8$, $C_3$-$C_6$cycloalkyl or $C_3$-$C_6$cycloalkyl substituted by halogen, —$OR_8$, —$OR_9$ or by $C_1$-$C_2$alkyl.

Of this preferred group, special mention should be made of those compounds wherein $R_1$ is fluorine, chlorine, methyl, trifluoromethyl or methoxy;

$R_2$ and $R_4$ independently of one another are hydrogen, fluorine, chlorine, methyl or methoxy;

$R_3$ is hydrogen;

$R_5$ is hydrogen, fluorine, chlorine, methyl, trifluoromethyl or methoxy; and

X, Y and Z independently of one another are hydrogen, methyl, cyclopropyl, 2-fluorocyclopropyl, 2,3-difluorocyclopropyl, 2-chlorocyclopropyl, 2,3-dichlorocyclopropyl, 1-methylcyclopropyl, 2-methylcyclopropyl, 2,3-dimethylcyclopropyl, cyclopentyl, fluorine, chlorine, trifluoromethyl or methoxy.

Prominent among the compounds of formula I on account of their good activity are especially those compounds wherein X is $C_3$-$C_6$cycloalkyl or $C_3$-$C_6$cycloalkyl substituted by halogen, —$OR_8$, —$OR_9$, —$SR_8$, —$SR_9$ or by $C_1$-$C_4$alkyl, preferably cyclopropyl, 1-methylcyclopropyl, 2-fluorocyclopropyl, 2,3-difluorocyclopropyl, 2-chlorocyclopropyl, 2,3-dichlorocyclopropyl, 2-methylcyclopropyl or 2,3-dimethylcyclopropyl, but especially cyclopropyl.

A preferred sub-group of compounds of formula I according to the invention consists of the compounds of formula Ia

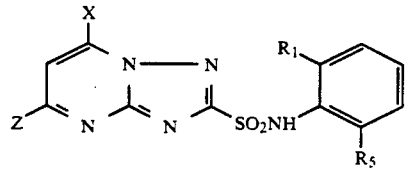

wherein $R_1$ is halogen, phenyl, O-phenyl, $C_1$-$C_4$alkyl, $C_1$-$C_4$-haloalkyl, —$OR_8$, —$OR_9$, nitro, hydroxy, cyano, —$SR_6$, —$SOR_6$, —$SO_2R_6$, —$SR_8$, —$SOR_8$, —$SO_2R_8$, —$SO_3R_8$, —$SR_9$, —$SOR_9$, —$SO_2R_9$, —$SO_2NR_{10}(R_{10})$, —$SO_3R_9$, —$COOR_7$, —$CONHR_9$, —$CONR_9(R_9)$, formyl,

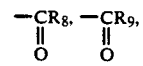

—$NH_2$, —$NHR_9$ or —$NR_9(R_9)$;

$R_5$ is hydrogen, halogen, phenyl, O-phenyl, $C_1$-$C_4$alkyl, $C_1$-$C_4$haloalkyl, —$OR_8$, —$OR_9$, nitro, hydroxy, cyano, —$SR_6$, —$SOR_6$, —$SO_2R_6$, —$SR_8$, —$SOR_8$, —$SO_3R_8$, —$SR_9$, —$SOR_9$, —$SO_2R_9$, —$SO_2NR_{10}(R_{10})$, —$SO_3R_9$, —$COOR_7$, —$CONHR_9$, —$CONR_9(R_9)$, formyl,

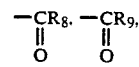

—$NH_2$, —$NHR_9$ or —$NR_9(R_9)$;

$R_6$ is hydrogen, phenyl, benzyl, $C_2$-$C_4$alkenyl, $C_2$-$C_4$alkynyl, or $C_1$-$C_4$alkyl substituted by —$OR_9$;

$R_7$ is $C_1$-$C_4$alkyl, $C_2$-$C_4$alkenyl, $C_2$-$C_4$alkynyl, phenyl or benzyl;

$R_8$ is $C_1$-$C_4$haloalkyl;

$R_9$ is $C_1$-$C_4$alkyl;

$R_{10}$ is hydrogen or $C_1$-$C_4$alkyl;

X and Z independently of one another are hydrogen, $C_1$-$C_4$alkyl, $C_1$-$C_4$haloalkyl, phenylthio, benzylthio, hydroxy, halogen, —$OR_8$, —$OR_9$, $C_1$-$C_4$alkyl substituted by —$OR_9$, $C_1$-$C_4$alkyl substituted by —$OR_8$, or —$NH_2$, —$NHR_9$, —$NR_9(R_9)$, $C_3$-$C_6$cycloalkyl or $C_3$-$C_6$cycloalkyl substituted by halogen, —$OR_8$, —$OR_9$, —$SR_8$, —$SR_9$ or by $C_1$-$C_4$alkyl; with the proviso that at least one of the substituents X and Z is $C_3$-$C_6$cycloalkyl or $C_3$-$C_6$cycloalkyl substituted by halogen, —$OR_8$, —$OR_9$, —$SR_8$, —$SR_9$ or by $C_1$-$C_4$alkyl.

Of the compounds of formula Ia, preference is given to those wherein $R_1$ is halogen, nitro, $C_1$-$C_4$alkyl, $C_1$-$C_4$haloalkyl, —$OR_8$, —$OR_9$, hydroxy, cyano or —$COOR_7$;

$R_5$ is hydrogen, halogen, nitro, $C_1$-$C_4$alkyl, $C_1$-$C_4$-haloalkyl, —$OR_8$, —$OR_9$, hydroxy, cyano or —$COOR_7$; and X and Z independently of one another are hydrogen, $C_1$-$C_4$alkyl, $C_1$-$C_4$haloalkyl, $C_1$-$C_4$alkyl substituted by —$OR_9$, $C_1$-$C_4$alkyl substituted by —$OR_8$, or halogen, $C_3$-$C_6$cycloalkyl or $C_3$-$C_6$cycloalkyl substituted by halogen, —$OR_8$, —$OR_9$, —$SR_8$, —$SR_9$ or by $C_1$-$C_4$alkyl.

Prominent on account of their good biological activity are especially those compounds of formula Ia wherein $R_1$ is halogen, nitro, $C_1$-$C_4$alkyl, $C_1$-$C_4$haloalkyl, —$OR_8$, —$OR_9$, hydroxy, cyano or —$COOR_7$;

$R_5$ is hydrogen, halogen, nitro, $C_1$-$C_4$alkyl, $C_1$-$C_4$haloalkyl, —$OR_8$, —$OR_9$, hydroxy, cyano or —$COOR_7$; and X and Z independently of one another are hydrogen, $C_1$-$C_4$alkyl, $C_1$-$C_4$haloalkyl, halogen, $C_3$-$C_6$cycloalkyl or $C_3$-$C_6$cycloalkyl substituted by halogen, —$OR_8$, —$OR_9$, —$SR_8$, —$SR_9$ or by $C_1$-$C_4$alkyl.

Of this group, preference is given to those compounds of formula Ia wherein $R_1$ is halogen, nitro, $C_1$-$C_2$alkyl, $C_1$-$C_2$haloalkyl, —$OR_8$, —$OR_9$, hydroxy, cyano or —$COOR_7$;

$R_5$ is hydrogen, halogen, nitro, $C_1$-$C_2$alkyl, $C_1$-$C_2$haloalkyl, —$OR_8$, —$OR_9$, hydroxy, cyano or —$COOR_7$;

$R_7$ is $C_1$-$C_2$alkyl, $C_2$-$C_3$alkenyl, $C_2$-$C_3$alkynyl, phenyl or benzyl;

$R_8$ is $C_1$-$C_2$haloalkyl;

$R_9$ is $C_1$-$C_2$alkyl; and

X and Z independently of one another are hydrogen, $C_1$-$C_2$alkyl, $C_1$-$C_2$haloalkyl, halogen, $C_3$-$C_6$cycloalkyl or $C_3$-$C_6$cycloalkyl substituted by halogen, —$OR_8$, —$OR_9$ or by $C_1$-$C_2$alkyl.

In a further sub-group of compounds of formula Ia deserving special mention, $R_1$ is fluorine, chlorine, methyl, trifluoromethyl or methoxy;

$R_5$ is hydrogen, fluorine, chlorine, methyl, trifluoromethyl or methoxy; and

X and Z independently of one another are hydrogen, methyl, cyclopropyl, 1-methylcyclopropyl, 2-fluorocyclopropyl, 2,3-difluorocyclopropyl, 2-chlorocyclopropyl, 2,3-dichlorocyclopropyl, 2-methylcyclopropyl, 2,3-dimethylcyclopropyl, cyclopentyl, fluorine, chlorine or methoxy.

Most especially prominent groups of compounds of formula Ia are those wherein $R_1$ is fluorine, chlorine, methyl or trifluoromethyl;

$R_5$ is hydrogen, chlorine, methyl or trifluoromethyl; and

X and Z independently of one another are hydrogen, cyclopropyl, 1-methylcyclopropyl, 2-fluorocyclopropyl, 2,3-difluorocyclopropyl, 2-chlorocyclopropyl, 2,3-dichlorocyclopropyl, 2-methylcyclopropyl, 2,3-dimethylcyclopropyl, methyl, methoxy, fluorine or chlorine.

Prominent among this preferred sub-group on account of their good biological activity are those compounds wherein X is cyclopropyl.

The following may be mentioned as preferred individual compounds within the scope of formula I:

5-methyl-7-cyclopropyl-N-(2,6-dichlorophenyl)-1,2,4-triazolo[1,5-a]pyrimidine-2-sulfonamide, 5-methyl-7-cyclopropyl-N-(2,6-difluorophenyl)-1,2,4-triazolo[1,5-a]pyrimidine-2-sulfonamide;

7-methyl-5-cyclopropyl-N-(2,6-dichlorophenyl)-1,2,4-triazolo[1,5-a]pyrimidine-2-sulfonamide, 5-cyclopropyl-7-trifluoromethyl-N-(2,6-dichlorophenyl)-1,2,4-triazolo[1,5-a]pyrimidine-2-sulfonamide, and 5-methyl-7-cyclobutyl-N-(2,6-dichlorophenyl)-1,2,4-triazolo[1,5-a]pyrimidine-2-sulfonamide.

The compounds of formula I are prepared by reacting a primary amine of formula II

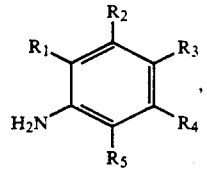

wherein $R_1$, $R_2$, $R_3$, $R_4$ and $R_5$ are as defined under formula I, in the presence of a base, with a triazolopyrimidinylsulfonyl chloride of formula III

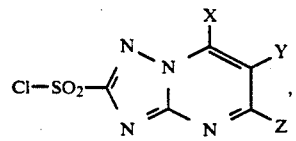

wherein X, Y and Z are as defined under formula I.

The process according to the invention is advantageously carried out in an inert solvent at a temperature of from −20° C. to the boiling point of the reaction mixture. The temperatures are usually from +15° C. to +120° C., preferably from +20° C. to +80° C. Suitable solvents are chlorinated hydrocarbons, such as methylene chloride, chloroform, carbon tetrachloride, trichloroethane, tetrachloroethane, chlorobenzene or dichlorobenzene; aromatic hydrocarbons, such as benzene, toluene or xylene; ethers, such as diethyl ether, diisopropyl ether, tetrahydrofuran, ethylene glycol dimethyl ether or dioxane; nitriles, such as acetonitrile or propionitrile; cyclohexane or pyridine. The reactions are generally slightly exothermic and can be carried out at room temperature. Suitable bases are especially tertiary amines, such as trimethylamine, triethylamine, N-methylmorpholine, quinuclidine, pyridine, 1,4-diazabicyclo[2.2.2]octane, 1,5-diazabicyclo[4.3.0]non-5-ene or 1,8-diazabicyclo[5.4.0]undec-7-ene.

The end products of formula I can be isolated by concentration and/or evaporation of the solvent and purified by recrystallisation or trituration of the solid residue in solvents in which they are not readily soluble, such as ethers, aromatic hydrocarbons or chlorinated hydrocarbons.

The primary amines of formula II can be obtained by reduction processes from the corresponding nitro compounds of formula IV

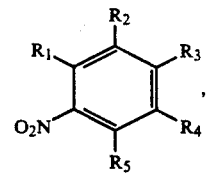

wherein $R_1$, $R_2$, $R_3$, $R_4$ and $R_5$ are as defined under formula I.

All the customary processes described in the literature can be used for the reduction of the nitro compounds of formula IV to the amino compounds of formula II. For example, the reduction can advantageously be carried out in an aqueous medium in the presence of iron, tin or zinc and hydrochloric acid. Further suitable methods are reduction processes using complex hydrides, such as lithium aluminium hydride, or catalytic reduction with hydrogen with the aid of platinum, palladium or nickel catalysts.

The nitro compounds of formula IV can be prepared by electrophilic substitution in nitration processes customary for aromatic compounds. The intermediates of formula II are known or they can be prepared analogously to known compounds.

The intermediates of formula III are novel compounds, and the present invention also includes them. The intermediates of formula III are obtainable by treating a compound of formula V

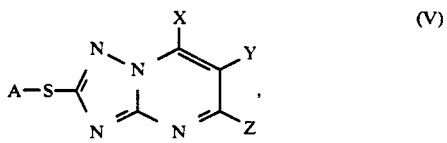

wherein X, Y and Z are as defined under formula I and A is hydrogen, isopropyl or benzyl, with chlorine in an aqueous acidic medium. The acid used is preferably acetic acid or an inorganic acid, especially hydrochloric acid. The treatment with chlorine is advantageously carried out at temperatures in the range of from $-25°$ C. to $20°$ C., preferably at from $-15°$ C. to $0°$ C. The treatment with chlorine is preferably carried out with the addition of dichloromethane to the medium.

The intermediates of formula V are novel compounds, and the present invention relates also to them. The intermediates of formula V can be prepared by reacting a compound of formula VI

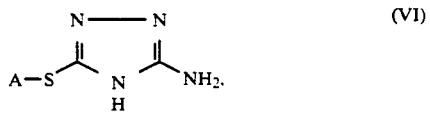

wherein A is hydrogen or benzyl, with a compound of formula VII

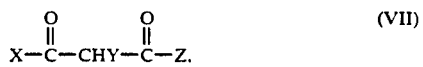

wherein X, Y and Z are as defined under formula I.

The compounds of formula I can also be prepared by reacting a compound of formula VIII

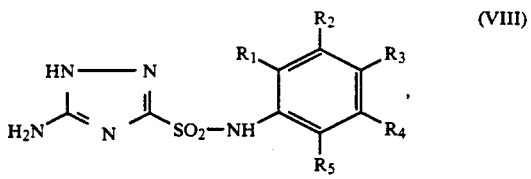

wherein $R_1$, $R_2$, $R_3$, $R_4$ and $R_5$ are as defined under formula I, with a compound of formula VII

wherein X, Y and Z are as defined under formula I. Such processes are described, for example, in U.S. Pat. No. 4,734,123.

The intermediates of formulae VI and VII are known or they can be prepared analogously to known methods.

The compound of formula VI wherein A is benzyl can be prepared, for example, in a manner known per se by reacting the compound of formula VI wherein A is hydrogen with benzyl chloride.

The reaction of a compound of formula VI or VIII with a compound of formula VII is advantageously carried out by first dissolving a compound of formula VI or VIII in a small amount of glacial acetic acid, with heating, and, after the addition of the compound of formula VII, heating the reaction mixture to reflux temperature.

The compounds of formula I can also be prepared by reacting a triazolopyrimidinylsulfonyl chloride of formula III

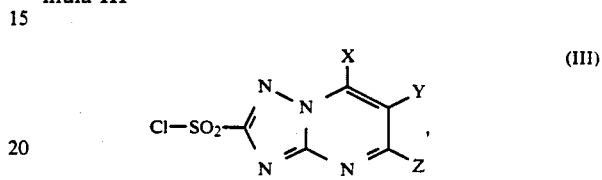

wherein X, Y and Z are as defined under formula I, with a compound of formula IX

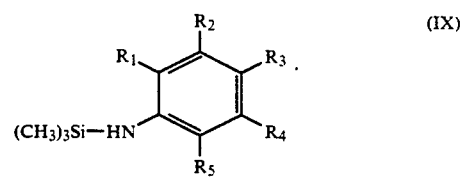

wherein $R_1$, $R_2$, $R_3$, $R_4$ and $R_5$ are as defined under formula I. Such processes are described, for example, in EP-A-0 343 752.

The compounds of formula I are generally used successfully at rates of application of from 0.001 to 5 kg/ha, especially from 0.005 to 3 kg/ha. The concentration required to achieve the desired effect can be determined by experiment. It is dependent on the type of action, the stage of development of the cultivated plant and of the weed, and also on the application (place, time, method) and, in dependence of those parameters, can vary within wide limits.

When used at relatively low rates of application, the compounds of formula I are distinguished by growth inhibiting and herbicidal properties, which render them excellently suitable for use in crops of useful plants, especially in cereals, cotton, soybeans, rape, maize and rice, their use in maize crops being very especially preferred.

The invention relates also to herbicidal and plant growth regulating compositions containing a novel compound of formula I, and to methods of inhibiting plant growth.

Plant growth regulators are substances that bring about agronomically desirable biochemical and/or physiological and/or morphological changes in/to the plant.

The active ingredients contained in the compositions according to the invention influence plant growth in different ways depending on the time of application, the concentration, the type of application and the environmental conditions. Plant growth regulators of formula I can, for example, inhibit the vegetative growth of plants. This type of action is valuable in the case of lawn areas, in the cultivation of ornamentals, in fruit plantations, in the case of roadside embankments and in sports fields and industrial sites, but also in the specific inhibition of side-shoots, as in the case of tobacco. In agriculture, inhibition of the vegetative growth of cereals leads, owing to strengthening of the stalk, to reduced lodging, and a similar agronomic effect is achieved in rape, sunflowers, maize and other cultivated plants. Moreover, by inhibiting the vegetative growth it is possible to increase the number of plants per unit area. Another field of application of growth inhibitors is the selective control of cover plants in plantations or widely spaced crops by greatly inhibiting the growth of the cover crops without killing them, so that competition with the main crop is eliminated but the agronomically positive effects, such as erosion prevention, fixing of nitrogen and loose soil structure, are preserved.

A method of inhibiting plant growth is to be understood as being a method of controlling a plant's natural development without changing its life-cycle, as determined by genetic characteristics, in the sense of mutation. The method of regulating growth is applied at a time in the plant's development that has to be determined for each individual case. The compounds of formula I can be applied pre- or postemergence, for example to the seeds or seedlings, to roots, tubers, stalks, leaves, blossoms or other parts of the plant. This can be done, for example, by applying the compound as such or in the form of a composition to the plants, and/or by treating the plant's nutrient medium (soil).

Various methods and techniques are suitable for the use of the compounds of formula I or of compositions containing them for regulating plant growth, for example the following:

i) Seed dressing a) Dressing the seeds with an active ingredient formulated as a wettable powder, by shaking in a container until the formulation is uniformly distributed over the surface of the seeds (dry dressing). Up to 4 g of compound of formula I (in the case of a 50% formulation: up to 8.0 g of wettable powder) are used per 1 kg of seed.

b) Dressing the seeds with an emulsifiable concentrate of the active ingredient or with an aqueous solution of the compound of formula I formulated as a wettable powder according to method a) (wet dressing).

c) Dressing by soaking the seeds for a period of from 1 to 72 hours in a liquor containing up to 1000 ppm of compound of formula I and, if desired, subsequently drying the seeds (seed soaking).

Seed dressing or treatment of the germinated seedling are naturally the preferred methods of application because the treatment with the active ingredient is then directed wholly at the target crop. From 4.0 g to 0.001 g of active ingredient are normally used per 1 kg of seed, although, depending on the method employed, which also allows the addition of other active ingredients or micronutrients, amounts that exceed or fall short of the specified concentration limits may be employed (repeat dressing).

ii) Controlled release of active ingredient

A solution of the active ingredient is applied to mineral granulate carriers or polymerised granulates (urea/formaldehyde) and allowed to dry. If required, a coating may be applied (coated granulates), which allows the active ingredient to be released in metered amounts over a specific period of time.

The compounds of formula I are used in unmodified form or, preferably, as compositions together with the adjuvants conventionally employed in the art of formulation, and are therefore formulated in known manner e.g. into emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfates or sulfonates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids.

These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives or aliphatic or cycloaliphatic alcohols, saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyethylene glycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in the art of formulation are described inter alia in the following publications:
"McCutcheon's Detergents and Emulsfiers Annual", MC Publishing Corp., Ridgewood, N.J., 1981;
H. Stache, "Tensid-Taschenbuch", 2nd edition, C. Hanser Verlag, Munich, Vienna, 1981; M. and J. Ash, "Encyclopedia of Surfactants", Vol. I-III, Chemical Publishing Co., New York, 1980–1981.

The agrochemical compositions generally contain 0.1 to 95%, preferably 0.1 to 80%, of a compound of formula I, 1 to 99.9% of a solid or liquid adjuvant and 0 to 25%, preferably 0.1 to 25%, of a surfactant.

Preferred formulations are composed in particular of the following constituents (%=percentage by weight):

| Emulsifiable concentrates: | |
|---|---|
| active ingredient: | 1 to 20%, preferably 5 to 10% |
| surfactant: | 5 to 30%, preferably 10 to 20% |
| liquid carrier: | 50 to 94%, preferably 70 to 85% |
| Dusts: | |
| active ingredient: | 0.1 to 10%, preferably 0.1 to 1% |
| solid carrier: | 99.9% to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powder: | |
| active ingredient: | 0.5 to 90%, preferably 1 to 80% |
| surfactant: | 0.5 to 20%, preferably 1 to 15% |
| solid carrier: | 5 to 99%, preferably 15 to 90% |
| Granulates: | |
| active ingredient: | 0.5 to 30%, preferably 3 to 15% |
| solid carrier: | 99.5 to 70%, preferably 97 to 85%. |

Whereas commercial products will preferably be formulated as concentrates, the end user will normally employ dilute formulations. The formulations can be diluted to a concentration as low as 0.001% active ingredient. The rates of application are normally from 0.001 to 5 kg a.i./ha, preferably from 0.005 to 3 kg a.i./ha.

The compositions may also contain further auxiliaries such as stabilisers, antifoams, viscosity regulators, binders, tackifiers as well as fertilisers or other active ingredients for obtaining special effects.

FORMULATION EXAMPLES

Example F1: Formulation Examples for active ingredients of formula I (throughout, percentages are by weight)

| a) Wettable powders | a) | b) | c) |
|---|---|---|---|
| compound no. 1.1 | 20% | 50% | 0.5% |
| sodium lignosulfonate | 5% | 5% | 4% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | 10% | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| b) Emulsifiable concentrate | a) | b) |
|---|---|---|
| compound no. 1.1 | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| c) Dusts | a) | b) |
|---|---|---|
| compound no. 1.2 | 0.1% | 1% |
| talcum | 99.9% | — |

| c) Dusts | a) | b) |
| --- | --- | --- |
| kaolin | — | 99% |

Ready-for-use dusts are obtained by mixing the active ingredient with the carrier and grinding the mixture in a suitable mill.

| d) Extruder granulate | a) | b) |
| --- | --- | --- |
| compound no. 1.1 | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is moistened with water. The mixture is extruded and then dried in a stream of air.

| e) Coated granulate | |
| --- | --- |
| compound no. 1.1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| f) Suspension concentrate | a) | b) |
| --- | --- | --- |
| compound no. 1.2 | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| g) Salt solution | |
| --- | --- |
| compound no. 1.2 | 5% |
| isopropylamine | 1% |
| octylphenol polyethylene glycol ether (78 moles of ethylene oxide) | 3% |
| water | 91% |

PREPARATION EXAMPLES

Example P1

Preparation of 2-benzylthio-5-methyl-7-cyclopropyl-1,2,4-triazolo-[1,5-a]pyrimidine (compound no. 2.1) and 2-benzylthio-5-cyclopropyl-7-methyl-1,2,4-triazolo[1,5-a]pyrimidine (compound no. 2.2)

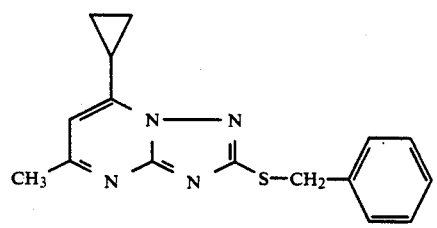
(2.1)

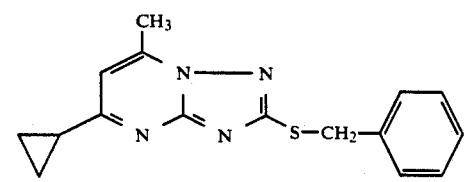
(2.2)

41.5 g of 3-amino-5-benzylthio-1,2,4-triazole are dissolved in a small amount of hot glacial acetic acid and heated under reflux together with 30 g of 1-cyclopropyl-1,3-butanedione. After about one hour, the reaction solution is concentrated in vacuo and water is added to the residue. The resulting dark resin is taken up in ethyl acetate and the ethyl acetate phase is separated off, dried over sodium sulfate and concentrated by evaporation. The residue is purified on a silica gel column (eluant: ethyl acetate/hexane 1:1), yielding the title compounds A and B:

1st fraction 20 g m.p.+101° to +103° C. (compound no. 2.2)

2nd fraction 39 g m.p. +84° to +86° C. (compound no. 2.1)

Example P2

Preparation of 2-benzylthio-7-cyclopropyl-1,2,4-triazolo[1,5-a]pyrimidine (compound no. 2.20)

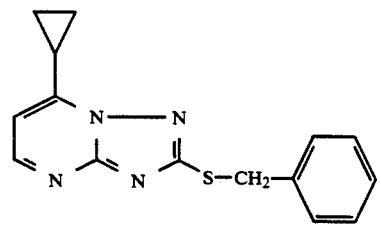
(2.20)

20 g of 3-amino-5-benzylthio-1,2,4-triazole together with 17 g of the potassium salt of 1-cyclopropyl-1,3-butanedione (obtained from the condensation reaction of acetylcyclopropane with formic acid ethyl ester in diethyl ether and potassium tert.-butanolate) and 0.05 mol of sodium methanolate are heated at boiling point for 3 hours in 300 ml of absolute ethanol. The reaction mixture is then concentrated in vacuo and water is added to the residue. After acidification with concentrated acetic acid, the resulting product is separated off, dried and recrystallised from methylene chloride/n-hexane, yielding 7 g of 2-benzylthio-7-cyclopropyl-1,2,4-triazolo[1,5-a]pyrimidine (compound no. 2.20) having a melting point of from +112° to +114° C.

Example P3

Preparation of 5-cyclopropyl-7-methyl-1,2,4-triazolo[1,5-a]pyrimidin-2-yl-sulfochloride (compound no. 3.2)

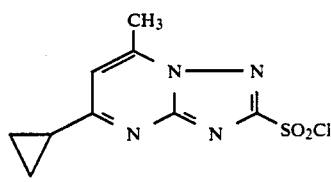
(3.2)

14 g of 2-benzylthio-5-cyclopropyl-7-methyl-1,2,4-triazolo[1,5-a]pyrimidine in 200 ml of dichloromethane and 200 ml of water are mixed with 10 ml of concentrated hydrochloric acid and stirred vigorously. 13.5 g of chlorine gas are introduced at from 0° C. to −3° C. within a period of about 20 minutes. After subsequently stirring for about half an hour without cooling, the organic phase is separated off, washed with water and dried over sodium sulfate. Concentration by evaporation in vacuo yields a dark oil, which is stirred thoroughly several times with petroleum ether. The petroleum ether is decanted off and the resulting viscous residue is dried. 11.5 g of 5-cyclopropyl-7-methyl-1,2,4-triazolo[1,5-a]pyrimidin-2-yl-sulfochloride (compound no. 3.2) are obtained in the form of a dark oil (crude product), which is suitable for the further reactions. The proton resonance spectrum confirms the constitution of the product obtained.

Example P4

Preparation of 5-methyl-7-cyclopropyl-1,2,4-triazolo[1,5-a]pyrimidin-2-yl-sulfochloride (compound no. 3.1)

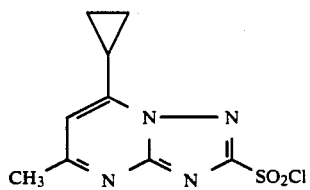
(3.1)

35 g of 2-benzylthio-5-methyl-7-cyclopropyl-1,2,4-triazolo[1,5-a]pyrimidine in 200 ml of dichloromethane are stirred with 300 ml of water and 20 ml of concentrated hydrochloric acid. 33.5 g of chlorine gas are introduced into the mixture at from 0° C. to −3° C. After about 30 minutes, the introduction is complete and the reaction mixture is then stirred for about 20 minutes without cooling. After dilution with water, the organic phase is separated off, dried over sodium sulfate and concentrated by evaporation in vacuo. The resulting oil is washed with several portions of petroleum ether. Drying yields 5-methyl-7-cyclopropyl-1,2,4-triazolo[1,5-a]pyrimidin-2-yl-sulfochloride (compound no. 3.1) in the form of a crude product, which is suitable for the further reactions. Yield: 28 g of dark oil.

Example P5

Preparation of 5-cyclopropyl-7-methyl-N-(2,6-dichlorophenyl)-1,2,4-triazolo[1,5-a]pyrimidine-2-sulfonamide (compound no. 1.2)

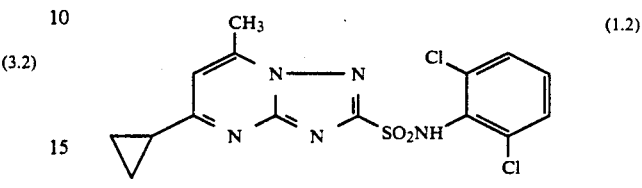
(1.2)

5.75 g of 5-cyclopropyl-7-methyl-1,2,4-triazolo[1,5-a]pyrimidin-2-yl-sulfochloride are added to a solution of 3.5 g of 2,6-dichloroaniline in 15 ml of anhydrous pyridine, and the mixture is then stirred at room temperature for 20 hours. After the addition of 200 ml of water and 20 ml of ethyl acetate, the pH of the reaction mixture is adjusted to pH 3 with concentrated hydrochloric acid. The resulting product is filtered off and the filtration residue is washed with water and n-hexane. Drying yields 6 g of 5-cyclopropyl-7-methyl-N-(2,6-dichlorophenyl)-1,2,4-triazolo[1,5-a]pyrimidine-2-sulfonamide (compound no. 1.2) having a melting point of +255° C. (decomp.).

Example P6

Preparation of 5-methyl-7-cyclobutyl-N-(2,6-dichlorophenyl)-1,2,4-triazolo[1,5-a]pyrimidine-2-sulfonamide (compound no. 1.25)

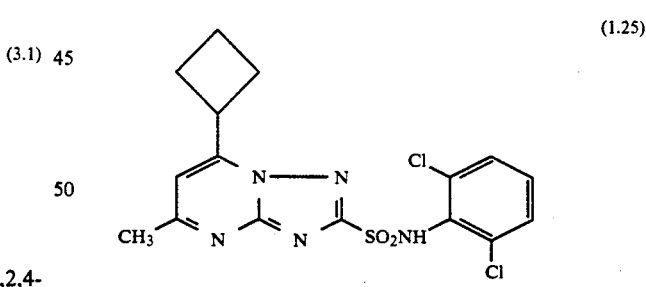
(1.25)

With the exclusion of moisture, 4.9 g of 5-methyl-7-cyclobutyl-1,2,4-triazolo[1,5-a]pyrimidin-2-yl-sulfochloride are dissolved in 50 ml of acetonitrile and stirred with 4.2 g of N-trimethylsilyl-2,6-dichloroaniline and 0.2 ml of dimethyl sulfoxide until the reaction is complete. After filtering and washing with acetonitrile, the filtrate is concentrated by evaporation and then triturated with water, yielding 1.8 g of 5-methyl-7-cyclobutyl-N-(2,6-dichlorophenyl)-1,2,4-triazolo[1,5-a]pyrimidine-2-sulfonamide (compound no. 1.25) having a melting point of +260° C.

Example P7

Preparation of 5-methyl-7-cyclopentyl-N-(2,6-dichlorophenyl)-1,2,4-triazolo[1,5-a]pyrimidine-2-sulfonamide (compound no. 1.85)

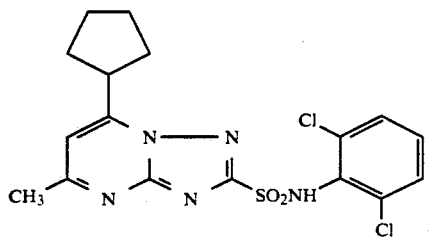

(1.85)

4 g of N-2,6-dichlorophenyl-5-amino-1,2,4-triazolo-3-yl-sulfonamide are stirred for 10 hours at room temperature and for one hour at +100° C. in 10 ml of dimethyl sulfoxide and 15 ml of glacial acetic acid with 4 g of 1-cyclopentylbutane-1,3-dione. Precipitation of the product by the addition of water and recrystallisation from glacial acetic acid yield 4 g of 5-methyl-7-cyclopentyl-N-(2,6-dichlorophenyl)-1,2,4-triazolo[1,5-a]pyrimidine-2-sulfonamide (compound no. 1.85) having a melting point of from +245° to +246° C.

The compounds of formula I and the intermediates of formulae III and V listed in the following Tables are prepared analogously.

TABLE 1

(I)

| Comp. no. | X | Y | Z | $R_1$ | $R_2$ | $R_3$ | $R_4$ | $R_5$ | m.p. [°C.] |
|---|---|---|---|---|---|---|---|---|---|
| 1.1 | cyclopropyl | H | $CH_3$ | Cl | H | H | H | Cl | +229 to +231 (decomp.) |
| 1.2 | $CH_3$ | H | cyclopropyl | Cl | H | H | H | Cl | +255 (decomp.) |
| 1.3 | cyclopropyl | H | cyclopropyl | Cl | H | H | H | Cl | +231 to +234 (decomp.) |
| 1.4 | $CF_3$ | H | cyclopropyl | Cl | H | H | H | Cl | +260 (decomp.) |
| 1.5 | cyclopropyl | H | H | Cl | H | H | H | Cl | +260 (decomp.) |
| 1.6 | cyclopropyl | H | $CF_3$ | Cl | H | H | H | Cl | |
| 1.7 | cyclopropyl | H | $CH_2CH_3$ | Cl | H | H | H | Cl | |
| 1.8 | $CF_3$ | H | cyclopropyl | Cl | H | H | H | Cl | |

TABLE 1-continued (I)

| Comp. no. | X | Y | Z | R$_1$ | R$_2$ | R$_3$ | R$_4$ | R$_5$ | m.p.[°C.] |
|---|---|---|---|---|---|---|---|---|---|
| 1.9 | CH$_2$CH$_3$ | H | cyclopropyl | Cl | H | H | H | Cl | +241 to +244 |
| 1.10 | C$_3$H$_7$(n) | H | cyclopropyl | Cl | H | H | H | Cl | |
| 1.11 | C$_3$H$_7$(i) | H | cyclopropyl | Cl | H | H | H | Cl | +236 to +238 |
| 1.12 | C$_4$H$_9$(tert.) | H | cyclopropyl | Cl | H | H | H | Cl | +263 (decomp.) |
| 1.13 | CH$_2$—OCH$_3$ | H | cyclopropyl | Cl | H | H | H | Cl | |
| 1.14 | Cl | H | cyclopropyl | Cl | H | H | H | Cl | |
| 1.15 | OCH$_3$ | H | cyclopropyl | Cl | H | H | H | Cl | |
| 1.16 | 2,2-difluorocyclopropyl | H | H | Cl | H | H | H | Cl | |
| 1.17 | CF$_3$ | H | cyclopentyl | Cl | H | H | H | Cl | |
| 1.18 | —OC$_2$H$_5$ | H | cyclopropyl | Cl | H | H | H | Cl | |
| 1.19 | OH | H | cyclopropyl | Cl | H | H | H | Cl | |

TABLE 1-continued (I)

| Comp. no. | X | Y | Z | $R_1$ | $R_2$ | $R_3$ | $R_4$ | $R_5$ | m.p.[°C.] |
|---|---|---|---|---|---|---|---|---|---|
| 1.20 | H | H | cyclopropyl | Cl | H | H | H | Cl | |
| 1.21 | —COOCH₃ | H | cyclopropyl | Cl | H | H | H | Cl | |
| 1.22 | cyclohexyl | H | CH₂CH₃ | Cl | H | H | H | Cl | |
| 1.23 | 2-methylcyclopropyl | H | CH₃ | Cl | H | H | H | Cl | |
| 1.24 | OCH₂CHCl₂ | H | cyclopropyl | Cl | H | H | H | Cl | |
| 1.25 | cyclobutyl | H | CH₃ | Cl | H | H | H | Cl | |
| 1.26 | 2,3-dimethylcyclopropyl | H | CH₃ | Cl | H | H | H | Cl | |
| 1.27 | CH₃ | H | 2,3-dichlorocyclopropyl | Cl | H | H | H | Cl | |
| 1.28 | NH₂ | H | cyclopropyl | Cl | H | H | H | Cl | |
| 1.29 | NHCH₃ | H | cyclopropyl | Cl | H | H | H | Cl | |

TABLE 1-continued
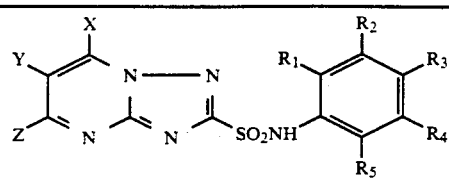
(I)
| Comp. no. | X | Y | Z | R₁ | R₂ | R₃ | R₄ | R₅ | m.p.[°C] |
|---|---|---|---|---|---|---|---|---|---|
| 1.30 | N(C₂H₅)₂ | H | △ | Cl | H | H | H | Cl | |
| 1.31 | △ | H | CH₃ | Cl | H | H | H | CH₃ | |
| 1.32 | △ | H | CF₃ | Cl | H | H | H | F | |
| 1.33 | △ | H | SCH₃ | Cl | H | H | H | Cl | |
| 1.34 | △ | H | Cl | Cl | H | H | H | OCH₃ | |
| 1.35 | △ | H | CH₃ | Cl | H | H | H | CF₃ | |
| 1.36 | △ | CH₃ | CH₃ | Cl | H | H | H | NO₂ | |
| 1.37 | △ | Cl | CH₃ | Cl | H | H | H | OH | |
| 1.38 | CH₃ | H | △ | CH₃ | CH₃ | H | CH₃ | H | |
| 1.39 | CH₃ | H | △ | F | H | Cl | OCH₃ | H | |
| 1.40 | CH₃ | H | △ | Br | H | H | COOCH₃ | H | |
| 1.41 | CH₃ | CH₃ | △ | H | Cl | H | H | Cl | |

TABLE 1-continued
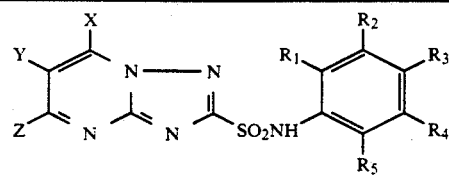
| Comp. no. | X | Y | Z | R₁ | R₂ | R₃ | R₄ | R₅ | m.p.[°C.] |
|---|---|---|---|---|---|---|---|---|---|
| 1.42 | CH₃ | CF₃ | △ | H | H | F | COO-C₆H₅ | Cl | |
| 1.43 | CH₃ | OCH₃ | △ | H | H | Br | H | Cl | |
| 1.44 | CH₃ | △ | △ | H | H | H | H | CHO | |
| 1.45 | CH₃ | Br | △ | H | H | H | H | CN | |
| 1.46 | CH₃ | H | △ | H | H | H | H | NH₂ | |
| 1.47 | CH₃ | H | △ | Cl | H | H | H | SCH₃ | |
| 1.48 | CH₃ | H | △ | Cl | H | H | H | SOCH₃ | |
| 1.49 | CH₃ | H | △ | Cl | H | H | H | SO₂CH₃ | |
| 1.50 | CH₃ | H | △ | Cl | H | H | H | SO₃CH₃ | |
| 1.51 | CH₃ | H | △ | Cl | H | H | H | CONHCH₃ | |
| 1.52 | CH₃ | H | △ | Cl | H | H | H | CON(CH₃)₂ | |

TABLE 1-continued (I)

| Comp. no. | X | Y | Z | R₁ | R₂ | R₃ | R₄ | R₅ | m.p.[°C.] |
|---|---|---|---|---|---|---|---|---|---|
| 1.53 | CH₃ | H | △ | Cl | H | H | H | —C(=O)CH₃ | |
| 1.54 | CH₃ | H | △ | Cl | H | H | H | NHCH₃ | |
| 1.55 | CH₃ | H | △ | Cl | H | H | H | N(CH₂CH₃)₂ | |
| 1.56 | H | H | △ | F | H | H | H | H | |
| 1.57 | H | H | △ | C₆H₅ | H | H | H | H | |
| 1.58 | H | H | △ | —O—C₆H₅ | H | H | H | H | |
| 1.59 | H | H | △ | CH₃ | H | H | H | H | |
| 1.60 | H | | △ | SCH₂CHCl₂ | C₂H₅ | H | H | H | |
| 1.61 | H | | △ | CH₃ | CF₃ | H | H | H | |
| 1.62 | H | | △ | C₂H₅ | CH₂CF₃ | H | H | H | |
| 1.63 | H | | △ | C₃H₇(n) | OCH₃ | H | H | H | |
| 1.64 | H | | △ | C₄H₉(tert). | OCH₂Cl | H | H | H | |

TABLE 1-continued

| Comp. no. | X | Y | Z | R₁ | R₂ | R₃ | R₄ | R₅ | m.p.[°C.] |
|---|---|---|---|---|---|---|---|---|---|
| 1.65 | cyclopropyl | H | H | NO₂ | H | H | H | H | |
| 1.66 | cyclopropyl | H | H | OH | H | H | H | H | |
| 1.67 | cyclopropyl | H | H | CN | H | H | H | H | |
| 1.68 | cyclopropyl | CH₃ | H | SCH₃ | H | H | H | H | |
| 1.69 | cyclopropyl | CF₃ | H | SOCH₃ | H | H | H | H | |
| 1.70 | cyclopropyl | SCH₃ | H | SO₂C₂H₅ | H | H | H | H | |
| 1.71 | —CH₂—CH₂—CH₂— | | cyclopropyl | Cl | H | H | H | Cl | |
| 1.72 | cyclopropyl | H | CH₃ | Br | H | H | H | Br | +239 to +241.5 |
| 1.73 | 2-methylcyclopropyl (CH₃) | H | CH₃ | F | H | H | H | F | +235 to +237 |
| 1.74 | cyclobutyl | H | CH₃ | Cl | H | H | CH₃ | Cl | +255 to +257 |
| 1.75 | —CH₂—OCH₃ | H | cyclopropyl | Cl | H | H | CH₃ | Cl | +250 to +254 |

TABLE 1-continued (I)

| Comp. no. | X | Y | Z | R₁ | R₂ | R₃ | R₄ | R₅ | m.p.[°C.] |
|---|---|---|---|---|---|---|---|---|---|
| 1.76 | cyclopropyl | H | —CH₂—OCH₃ | Cl | H | H | H | Cl | +194 to +196 |
| 1.77 | CH₃ | H | 2-methylcyclopropyl | Cl | H | H | H | Cl | +292.4 (decomp.) |
| 1.78 | CH₃ | H | cyclobutyl | Cl | H | H | H | Cl | +300 (decomp.) |
| 1.79 | cyclopropyl | —CH₂—CH₂—CH₂— | | Cl | H | H | H | Cl | +245 to +246 |
| 1.80 | 1-methylcyclopropyl | H | CH₃ | Cl | H | H | H | Cl | +253 to +256 |
| 1.81 | 1-methylcyclopropyl | H | CH₃ | F | H | H | H | F | +261 |
| 1.82 | CH₃ | H | cyclopropyl | F | H | H | H | F | +300 (decomp.) |
| 1.83 | cyclopropyl | H | CH₃ | F | H | H | H | F | +240 to +241 (decomp.) |
| 1.84 | 1-methylcyclopropyl | H | H | Cl | H | H | H | Cl | +260 (decomp.) |
| 1.85 | cyclopentyl | H | CH₃ | Cl | H | H | H | Cl | +245 to +246 |
| 1.86 | OCH₃ | H | cyclohexyl | Cl | H | H | H | Cl | +221 to +226 |

TABLE 1-continued (I)

| Comp. no. | X | Y | Z | R1 | R2 | R3 | R4 | R5 | m.p.[°C.] |
|---|---|---|---|---|---|---|---|---|---|
| 1.87 | 1-methylcyclopropyl | H | CH₃ | Cl | CH₃ | H | H | Cl | >300 |
| 1.88 | cyclopropyl | H | CH₃ | Cl | CH₃ | H | H | Cl | +244 to +246.5 |
| 1.89 | CH₃ | H | cyclopropyl | Cl | CH₃ | H | H | Cl | +282 to +286 |
| 1.90 | 1-methylcyclopropyl | H | CH₃ | Cl | CH₃ | H | H | Cl | >+300 |
| 1.91 | CH₃ | H | cyclopropyl | Br | H | H | H | Br | >+250 |
| 1.92 | 1-methylcyclopropyl | H | H | Br | H | H | H | Br | >+300 |
| 1.93 | OCH₃ | H | cyclopropyl | Cl | H | H | H | Cl | +206 to +209 |
| 1.94 | cyclopropyl | H | CH₃ | CF₃ | H | H | H | H | +171 to +174 |
| 1.95 | cyclopropyl | H | CH₃ | Cl | H | H | H | H | +191.5 to +173.5 |
| 1.96 | cyclopropyl | H | CH₃ | Cl | H | H | CF₃ | H | +190.4 to +143 |
| 1.97 | cyclopropyl | H | CH₃ | H | H | Cl | CF₃ | H | +257 to +259 |

TABLE 1-continued
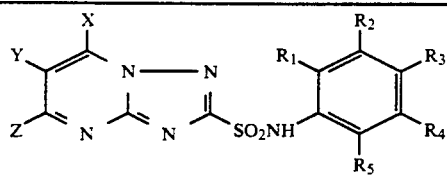
(I)
| Comp. no. | X | Y | Z | R₁ | R₂ | R₃ | R₄ | R₅ | m.p.[°C.] |
|---|---|---|---|---|---|---|---|---|---|
| 1.98 | 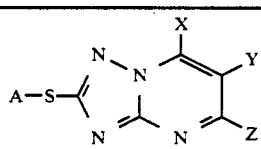 | H | CH₃ | F | H | | Cl | H | +217.8 to +219.5 |
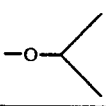
(V)
| Comp. no. | X | Y | Z | A | m.p.[°C.] |
|---|---|---|---|---|---|
| 2.1 | △ | H | CH₃ | Benzyl | +84 to +86 |
| 2.2 | CH₃ | H | △ | Benzyl | +101 to +103 |
| 2.3 | △ | H | △ | Benzyl | +96 to +98 |
| 2.4 | CF₃ | H | △ | Benzyl | +123 to +124 |
| 2.5 | △ | H | H | Benzyl | +82 to +86 |
| 2.6 | △ | H | CF₃ | Benzyl | |
| 2.7 | △ | H | CH₂CH₃ | Benzyl | +112 to +114 |
| 2.8 | CF₃ | H | △ | H | |
| 2.9 | CH₂CH₃ | H | △ | Benzyl | +84 to +85 |

-continued (V)

A—S structure with X, Y, Z substituents on triazolo-pyrimidine ring

| Comp. no. | X | Y | Z | A | m.p.[°C.] |
|---|---|---|---|---|---|
| 2.10 | C₃H₇(n) | H | cyclopropyl | Benzyl | |
| 2.11 | C₃H₇(i) | H | cyclopropyl | Benzyl | |
| 2.12 | C₄H₉(tert.) | H | cyclopropyl | Benzyl | +111 to +113 |
| 2.13 | CH₂—OCH₃ | H | cyclopropyl | Benzyl | |
| 2.14 | Cl | H | cyclopropyl | Benzyl | |
| 2.15 | OCH₃ | H | cyclopropyl | Benzyl | |
| 2.16 | 2,2-difluorocyclopropyl | H | H | Benzyl | |
| 2.17 | CF₃ | H | cyclopentyl | Benzyl | |
| 2.18 | —OC₂H₅ | H | cyclopropyl | Benzyl | |
| 2.19 | OH | H | cyclopropyl | Benzyl | |
| 2.20 | H | H | cyclopropyl | Benzyl | +112 to +114 |

-continued (V)

A—S-[triazolo-pyrimidine with X, Y, Z substituents]

| Comp. no. | X | Y | Z | A | m.p.[°C.] |
|---|---|---|---|---|---|
| 2.21 | —COOCH$_3$ | H | cyclopropyl | Benzyl | |
| 2.22 | cyclohexyl | H | CH$_2$CH$_3$ | Benzyl | |
| 2.23 | 1-methylcyclopropyl | H | CH$_3$ | Benzyl | |
| 2.24 | OCH$_2$CHCl$_2$ | H | cyclopropyl | Benzyl | |
| 2.25 | cyclobutyl | H | CH$_3$ | Benzyl | |
| 2.26 | 2,3-dimethylcyclopropyl | H | CH$_3$ | Benzyl | |
| 2.27 | CH$_3$ | H | 2,2-dichlorocyclopropyl | Benzyl | |
| 2.28 | NH$_2$ | H | cyclopropyl | Benzyl | |
| 2.29 | NHCH$_3$ | H | cyclopropyl | Benzyl | |
| 2.30 | N(C$_2$H$_5$)$_2$ | H | cyclopropyl | Benzyl | |
| 2.31 | cyclopropyl | H | CH$_3$ | H | |

-continued $$\text{(V)}$$

A—S structure with triazine-pyrimidine ring system bearing X, Y, Z substituents

| Comp. no. | X | Y | Z | A | m.p.[°C.] |
|---|---|---|---|---|---|
| 2.32 | cyclopropyl | H | CF$_3$ | H | |
| 2.33 | cyclopropyl | H | SCH$_3$ | H | |
| 2.34 | cyclopropyl | H | Cl | H | |
| 2.35 | cyclopropyl | C$_2$H$_5$ | CH$_3$ | H | |
| 2.36 | cyclopropyl | CH$_3$ | CH$_3$ | H | |
| 2.37 | cyclopropyl | Cl | CH$_3$ | H | |
| 2.38 | CH$_3$ | H | cyclopropyl | H | |
| 2.39 | CH$_3$ | C$_3$H$_7$(i) | cyclopropyl | H | |
| 2.40 | CH$_3$ | OCH$_2$CH$_3$ | cyclopropyl | H | |
| 2.41 | CH$_3$ | CH$_3$ | cyclopropyl | H | |
| 2.42 | CH$_3$ | CF$_3$ | cyclopropyl | H | |
| 2.43 | CH$_3$ | OCH$_3$ | cyclopropyl | H | |

-continued (V)

A—S—[triazolo-pyrimidine ring with X, Y, Z substituents]

| Comp. no. | X | Y | Z | A | m.p.[°C.] |
|---|---|---|---|---|---|
| 2.44 | CH₃ | cyclopropyl | cyclopropyl | H | |
| 2.45 | CH₃ | Br | cyclopropyl | H | |
| 2.46 | —CH₂—CH₂—CH₂— | | cyclopropyl | Benzyl | +93 to +94 |
| 2.47 | cyclopropyl | —CH₂—CH₂—CH₂— | | Benzyl | +113 to +114 |
| 2.48 | CH₃ | H | 1-methylcyclopropyl | Br | +76 to +77 |
| 2.49 | 1-methylcyclopropyl | H | CH₃ | Br | +97 to +100 |
| 2.50 | CH₃ | H | 2-methylcyclopropyl | Br | +100 to +102 |
| 2.51 | cyclopropyl | H | Cl | Br | +108 to +110 |
| 2.52 | cyclohexyl | H | CH₃ | Br | +97 to +98 |
| 2.53 | cyclopropyl | H | CH₂—OCH₃ | Br | +65 |
| 2.54 | CH₂—OCH₃ | H | cyclopropyl | Br | +113 to +116 |

-continued
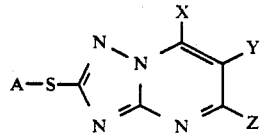
(V)
| Comp. no. | X | Y | Z | A | m.p.[°C.] |
|---|---|---|---|---|---|
| 2.55 |  | H | H | Br | +62 to +66 |
| 2.56 | CH$_3$ | H | 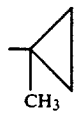 | Br | +76 to +77 |
| 2.57 | OCH$_3$ | H | 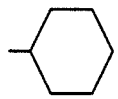 | Br | +151 to +154 |
| 2.58 | OCH$_3$ | H |  | Br | +130 |
| 2.59 | OH | H |  | Br | > +260 |
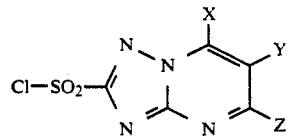
(III)
| Comp. no. | X | Y | Z | m.p.[°C.] |
|---|---|---|---|---|
| 3.1 |  | H | CH$_3$ | oil |
| 3.2 | CH$_3$ | H |  | oil |
| 3.3 |  | H |  | +127 to +130 |
| 3.4 | CF$_3$ | H |  | +78 to +81 |
| 3.5 |  | H | H | +100 to +103 |
-continued
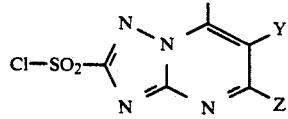
(III)
| Comp. no. | X | Y | Z | m.p.[°C.] |
|---|---|---|---|---|
| 3.6 |  | H | CF$_3$ | |
| 3.7 |  | H | CH$_2$CH$_3$ | +62 to +63 |
| 3.8 | H | H | 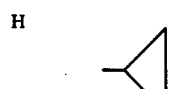 | +124 to +129 |
| 3.9 | CH$_2$CH$_3$ | H | 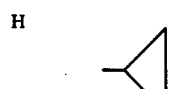 | +83 to +86 |

-continued (III)

Structure: Cl—SO₂-[triazine ring with X, Y, Z substituents]

| Comp. no. | X | Y | Z | m.p.[°C.] |
|---|---|---|---|---|
| 3.10 | C₃H₇(n) | H | cyclopropyl | |
| 3.11 | C₃H₇(i) | H | cyclopropyl | +121 |
| 3.12 | C₄H₉(tert.) | H | cyclopropyl | +123 |
| 3.13 | CH₂—OCH₃ | H | cyclopropyl | |
| 3.14 | Cl | H | cyclopropyl | +82 |
| 3.15 | OCH₃ | H | cyclopropyl | +125 to +130 |
| 3.16 | difluorocyclopropyl | H | H | |
| 3.17 | CF₃ | H | cyclopentyl | |
| 3.18 | —OC₂H₅ | H | cyclopropyl | |
| 3.19 | OH | H | cyclopropyl | |
| 3.20 | H | H | cyclopropyl | |

-continued (III)

| Comp. no. | X | Y | Z | m.p.[°C.] |
|---|---|---|---|---|
| 3.21 | —COOCH₃ | H | cyclopropyl | |
| 3.22 | cyclohexyl | H | CH₂CH₃ | |
| 3.23 | methylcyclopropyl | H | CH₃ | |
| 3.24 | OCH₂CHCl₃ | H | cyclopropyl | |
| 3.25 | cyclobutyl | H | CH₃ | |
| 3.26 | 2,3-dimethylcyclopropyl | H | CH₃ | |
| 3.27 | CH₃ | H | dichlorocyclopropyl | |
| 3.28 | NH₂ | H | cyclopropyl | |
| 3.29 | NHCH₃ | H | cyclopropyl | |
| 3.30 | N(C₂H₅)₂ | H | cyclopropyl | |
| 3.31 | cyclopropyl | H | SCH₃ | |

-continued $$\text{Cl-SO}_2\text{-[triazine]} \quad \text{(III)}$$

with substituents X, Y, Z on the fused pyrimidine ring.

| Comp. no. | X | Y | Z | m.p.[°C] |
|---|---|---|---|---|
| 3.32 | cyclopropyl | CH₃ | CH₃ | |
| 3.33 | cyclopropyl | Cl | CH₃ | |
| 3.34 | CH₃ | CF₃ | cyclopropyl | |
| 3.35 | CH₃ | OCH₃ | cyclopropyl | |
| 3.36 | CH₃ | cyclopropyl | cyclopropyl | |
| 3.36 | CH₃ | Br | cyclopropyl | |
| 3.37 | —CH₂—CH₂—CH₂— | | cyclopropyl | +152 to +153 |
| 3.38 | cyclopropyl | —CH₂—CH₂—CH₂— | | |
| 3.39 | 1-methylcyclopropyl | H | H | +151 to +156 |
| 3.40 | 2-methylcyclopropyl | H | CH₃ | oil |
| 3.41 | CH₃ | H | cyclobutyl | +91 to +95 |
| 3.42 | cyclopropyl | H | CH₂—OCH₃ | +90 to +95 |
| 3.43 | cyclobutyl | H | CH₃ | +68 to +75 |
| 3.44 | CH₂—OCH₃ | H | cyclopropyl | +73 to +77 |
| 3.45 | 1-methylcyclopropyl | H | CH₃ | |
| 3.46 | OCH₃ | H | cyclohexyl | |

BIOLOGICAL EXAMPLES

EXAMPLE B1

Preemergence Herbicidal Action

In a greenhouse, immediately after the test plants have been sown in seed trays, the surface of the soil is treated with an aqueous spray mixture in an amount corresponding to a rate of application of 4 kg of test compound/hectare. The seed trays are kept in the greenhouse at 22°–25° C. and 50–70% relative humidity.

After 3 weeks, the herbicidal action is evaluated according to a scale of nine ratings (1 = total damage, 9 = no action) in comparison with an untreated control group.

Ratings of from 1 to 4 (especially from 1 to 3) indicate good to very good herbicidal action. Ratings of from 6 to 9 (especially from 7 to 9) indicate good tolerance (especially in cultivated plants).

The compounds of Table 1 exhibit pronounced herbicidal activity in this test.

EXAMPLE B2

Postemergence Herbicidal Action (Contact Herbicide)

A number of weeds, both mono- and dicotyledonous, are sprayed postemergence (in the 4-to 6-leaf stage) with an aqueous active ingredient dispersion at a rate of 4 kg of test compound per hectare and kept at 24°–26° C. and 45–60% relative humidity. The test is evaluated 15 days after the treatment. In this test too, the compounds of Table 1 exhibit good herbicidal activity.

EXAMPLE B3

Herbicidal Action in Wild Rice (Paddy Rice)

The weeds Echinochloa crus galli and Monocharia vag., which occur in water, are shown in plastic beakers (surface: 60 cm$^2$; volume: 500 ml). After sowing, the beakers are filled with water up to the surface of the soil. 3 days after sowing, the water level is increased to slightly above the soil surface (3-5 mm). Application is effected 3 days after sowing by spraying the beakers with the test compounds. The rate of application corresponds to a concentration of 4 kg of active ingredient per hectare. The beakers are then kept in the greenhouse under optimum growth conditions for rice weeds, i.e. at 25°-30° C. and at high humidity.

The evaluation of the tests takes place 3 weeks after application. The compounds of Table 1 damage the weeds but not the rice.

EXAMPLE B4

Growth Inhibition of Tropical Cover Crops

The test plants Centrosema pubescens and Psophocarpus palustris are propagated by means of cuttings in 4 cm peat pots containing earth (45%), peat (45%) and Zonolite (10%). The cuttings are raised in a greenhouse at a day temperature of 27° C. and a night temperature of 23° C. The plants are illuminated for at least 14 hours/day with an intensity of at least 7000 lux.

About 50 days after the cuttings were taken, they are transplanted into 13 cm pots, 4-5 plants/pot. After a further 60 days, the plants are cut back to a height of about 15 cm and treated by spraying with an aqueous spray mixture at a concentration of 0.1 to 300 g of active ingredient/ha (usually as a 25% formulation). The amount of water applied is about 200 l/ha.

4 weeks after application, the weight of the new growth is determined and expressed as a percentage of the average of the untreated controls. The necrotic damage is given as a percentage of the total leaf area.

The new growth on the treated plants is markedly less than that on the untreated controls.

EXAMPLE B5

Growth Regulation of Soybeans

Test plants of the Williams variety are sown in 11 cm clay pots containing earth (45%), peat (45%) and Zonolite (10%) and are raised in a climatic chamber at a day temperature of 24° C. and a night temperature of 19° C. The plants are illuminated for 16 hours per day with an intensity of about 350 micro-einsteins.

About 24 days after sowing, the plants are transplanted into 18 cm pots, 2 plants/pot. After a further 12 days, when the plants are in the 5-6 trefoil leaf stage, the test compound is applied at a concentration of 0.1 to 300 g of active ingredient/ha, usually as a 25% formulation and in an aqueous spray mixture. The amount of water applied is about 200 l/ha.

Evaluation is made about 4 weeks after application. The height of the new growth is measured and expressed as a percentage of the average of the untreated controls. The necrotic damage is given as a percentage of the total leaf area.

The treated plants exhibit markedly less new growth than do the untreated controls.

EXAMPLE B6

Growth inhibition of cereals

Test plants (summer barley of the Iban variety) are sown in 15 cm plastic pots containing sterile earth and raised in a climatic chamber at a day temperature of 10°-15° C. and a night temperature of 5°-10° C. The plants are illuminated for 13.5 hours per day with an intensity of about 25000 lux.

About 34 days after sowing, and after the plants have been thinned out to 4 plants/pot, the test compound is applied at a concentration of 0.1 to 300 g of active ingredient/ha, usually as a 25% formulation and in an aqueous spray mixture. The amount of water applied is about 500 l/ha. After application, the plants are placed in a greenhouse at a day temperature of at least 10° C. They are illuminated for at least 13.5 hours/day.

Evaluation is made about 28 days after the treatment. The height of the new growth is expressed as a percentage of the average of the untreated controls. The necrotic damage is given as a percentage of the total leaf area.

The treated plants exhibit a reduction in new growth in comparison with untreated controls.

EXAMPLE B7

Growth inhibition of grasses

A mixture of grasses (e.g. Poa, Festuca, Lolium, Bromus, Cynosurus) and clover (Trifolium pratense/repens) is sown in 15 cm plastic pots containing sterile earth and the plants are raised in a greenhouse at a day temperature of 21° C. and a night temperature of 17° C. The plants are illuminated for 13.5 hours/day with an intensity of at least 7000 lux. The emergent plants are cut back weekly to a height of about 6 cm. About 42 days after sowing and 1 day after the last cut, the test compound is applied at a concentration of 0.1 to 300 g of active ingredient/ha, usually as a 25% formulation and in an aqueous spray mixture. The amount of water applied is about 500 l/ha.

Evaluation is made about 3 weeks after treatment. The height of the new growth is measured and expressed as a percentage of the average of the untreated controls. The necrotic damage is given as a percentage of the total leaf area.

The tested compounds of Table 1 effect a reduction in new growth in comparison with untreated controls.

What is claimed is:

1. A compound of formula I $$\underset{Z}{\overset{X}{\underset{\|}{Y}}}\underset{N}{\overset{}{\underset{\|}{\bigvee}}}\underset{N}{\overset{N------N}{\underset{\|}{\bigvee}}}\underset{SO_2NH}{\overset{R_1}{\underset{R_5}{\bigvee}}}\underset{R_4}{\overset{R_2}{\underset{}{\bigvee}}}R_3 \quad (I)$$

wherein
$R_1$ is halogen, phenyl, O-phenyl, $C_1$-$C_4$alkyl, $C_1$-$C_4$haloalkyl, $-OR_8$, $-OR_9$, nitro, hydroxy, cyano, $-SR_6$, $-SOR_6$, $-SO_2R_6$, $-SR_8$, $-SOR_8$, $-SO_2R_8$, $-SO_3R_8$, $-SR_9$, $-SOR_9$, $-SO_2R_9$, $-SO_2NR_{10}(R_{10})$, $-SO_3R_9$, $-COOR_7$, $-CONHR_9$, $-CONR_9(R_9)$, formyl,

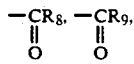

—NH$_2$, —NHR$_9$ or —NR$_9$(R$_9$);

R$_2$ and R$_4$ independently of one another are hydrogen, halogen, C$_1$-C$_4$alkyl, —COOR$_7$ or —OR$_9$;

R$_3$ is hydrogen or halogen;

R$_5$ is hydrogen, halogen, phenyl, O-phenyl, C$_1$-C$_4$alkyl, C$_1$-C$_4$haloalkyl, —OR$_8$, —OR$_9$, nitro, hydroxy, cyano, —SR$_6$, —SOR$_6$, —SO$_2$R$_6$, —SR$_8$, —SOR$_8$, —SO$_3$R$_8$, —SR$_9$, —SOR$_9$, —SO$_2$R$_9$, —SO$_2$NR$_{10}$(R$_{10}$), —SO$_3$R$_9$, —COOR$_7$, —CONHR$_9$, —CONR$_9$(R$_9$), formyl,

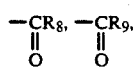

—NH$_2$, —NHR$_9$ or —NR$_9$(R$_9$);

R$_6$ is hydrogen, phenyl, benzyl, C$_2$-C$_4$alkenyl, C$_2$-C$_4$alkynyl, or C$_1$-C$_4$alkyl substituted by —OR$_9$;

R$_7$ is C$_1$-C$_4$alkyl, C$_2$-C$_4$alkenyl, C$_2$-C$_4$alkynyl, phenyl or benzyl;

R$_8$ is C$_1$-C$_4$haloalkyl;

R$_9$ is C$_1$-C$_4$alkyl;

R$_{10}$ is hydrogen or C$_1$-C$_4$alkyl;

X, Y and Z independently of one another are hydrogen, C$_1$-C$_4$alkyl, C$_1$-C$_4$haloalkyl, phenylthio, benzylthio, hydroxy, halogen, —OR$_8$, —OR$_9$, C$_1$-C$_4$alkyl substituted by —OR$_9$, C$_1$-C$_4$alkyl substituted by —OR$_8$, or —NH$_2$, —NHR$_9$, —NR$_9$(R$_9$), C$_3$-C$_6$cycloalkyl, C$_3$-C$_6$cycloalkyl substituted by halogen, —OR$_8$, —OR$_9$, —SR$_8$, —SR$_9$ or by C$_1$-C$_4$alkyl, with the proviso that at least one of the substituents X, Y and Z is C$_3$-C$_6$cycloalkyl or C$_3$-C$_6$cycloalkyl substituted by halogen, —OR$_8$, —OR$_9$, —SR$_8$, —SR$_9$ or by C$_1$-C$_4$alkyl; and the salts of those compounds.

2. A compound of formula I according to claim 1, wherein

R$_1$ is halogen, nitro, C$_1$-C$_4$alkyl, C$_1$-C$_4$haloalkyl, —OR$_8$, —OR$_9$, hydroxy, cyano or —COOR$_7$;

R$_5$ is hydrogen, halogen, nitro, C$_1$-C$_4$alkyl, C$_1$-C$_4$haloalkyl, —OR$_8$, —OR$_9$, hydroxy, cyano or —COOR$_7$; and X, Y and Z independently of one another are hydrogen, C$_1$-C$_4$alkyl, C$_1$-C$_4$haloalkyl, C$_1$-C$_4$alkyl substituted by —OR$_9$, C$_1$-C$_4$alkyl substituted by —OR$_8$, or halogen, C$_3$-C$_6$cycloalkyl or C$_3$-C$_6$cycloalkyl substituted by halogen, —OR$_8$, —OR$_9$, —SR$_8$, —SR$_9$ or by C$_1$-C$_4$alkyl.

3. A compound of formula I according to claim 1, wherein

R$_1$ is halogen, nitro, C$_1$-C$_2$alkyl, C$_1$-C$_2$haloalkyl, —OR$_8$, —OR$_9$, hydroxy, cyano or —COOR$_7$, R$_2$ and R$_4$ independently of one another are hydrogen, halogen, C$_1$-C$_2$alkyl, —COOR$_7$ or —OR$_9$;

R$_5$ is hydrogen, halogen, nitro, C$_1$-C$_2$alkyl, C$_1$-C$_2$haloalkyl, —OR$_8$, —OR$_9$, hydroxy, cyano or —COOR$_7$;

R$_7$ is C$_1$-C$_2$alkyl, C$_2$-C$_3$alkenyl, C$_2$-C$_3$alkynyl, phenyl or benzyl;

R$_8$ is C$_1$-C$_2$haloalkyl;

R$_9$ is C$_1$-C$_2$alkyl; and

X, Y and Z independently of one another are hydrogen, C$_1$-C$_2$alkyl, C$_1$-C$_2$haloalkyl, halogen, C$_1$-C$_4$alkyl substituted by —OR$_9$, C$_1$-C$_4$alkyl substituted by —OR$_8$, C$_3$-C$_6$cycloalkyl or C$_3$-C$_6$cycloalkyl substituted by halogen, —OR$_8$, —OR$_9$ or by C$_1$-C$_2$alkyl.

4. A compound of formula I according to claim 3, wherein

R$_1$ is fluorine, chlorine, methyl, trifluoromethyl or methoxy;

R$_2$ and R$_4$ independently of one another are hydrogen, fluorine, chlorine, methyl or methoxy;

R$_3$ is hydrogen;

R$_5$ is hydrogen, fluorine, chlorine, methyl, trifluoromethyl or methoxy; and

X, Y and Z independently of one another are hydrogen, methyl, cyclopropyl, 1-methylcyclopropyl, 2-fluorocyclopropyl, 2,3-difluorocyclopropyl, 2-chlorocyclopropyl, 2,3-dichlorocyclopropyl, 2-methylcyclopropyl, 2,3-dimethylcyclopropyl, cyclopentyl, fluorine, chlorine, trifluoromethyl or methoxy.

5. A compound of formula Ia

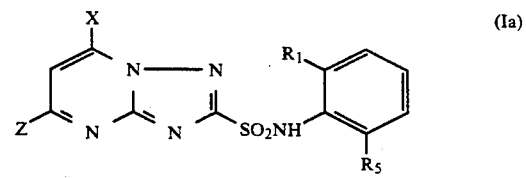

wherein

R$_1$ is halogen, phenyl, O-phenyl, C$_1$-C$_4$alkyl, C$_1$-C$_4$haloalkyl, —OR$_8$, —OR$_9$, nitro, hydroxy, cyano, —SR$_6$, —SOR$_6$, —SO$_2$R$_6$, —SR$_8$, —SOR$_8$, —SO$_2$R$_8$, —SO$_3$R$_8$, —SR$_9$, —SOR$_9$, —SO$_2$R$_9$, —SO$_2$NR$_{10}$(R$_{10}$), —SO$_3$R$_9$, —COOR$_7$, —CONHR$_9$, —CONR$_9$(R$_9$), formyl,

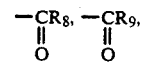

—NH$_2$, —NHR$_9$ or —NR$_9$(R$_9$);

R$_5$ is hydrogen, halogen, phenyl, O-phenyl, C$_1$-C$_4$alkyl, C$_1$-C$_4$haloalkyl, —OR$_8$, —OR$_9$, nitro, hydroxy, cyano, —SR$_6$, —SOR$_6$, —SO$_2$R$_6$, —SR$_8$, —SOR$_8$, —SO$_3$R$_8$, —SR$_9$, —SOR$_9$, —SO$_2$R$_9$, —SO$_2$NR$_{10}$(R$_{10}$), —SO$_3$R$_9$, —COOR$_7$, —CONHR$_9$, —CONR$_9$(R$_9$), formyl,

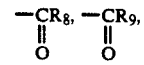

—NH$_2$, —NHR$_9$ or —NR$_9$(R$_9$);

R$_6$ is hydrogen, phenyl, benzyl, C$_2$-C$_4$alkenyl, C$_2$-C$_4$alkynyl, or C$_1$-C$_4$alkyl substituted by —OR$_9$;

R$_7$ is C$_1$-C$_4$alkyl, C$_2$-C$_4$alkenyl, C$_2$-C$_4$alkynyl, phenyl or benzyl;

R$_8$ is C$_1$-C$_4$haloalkyl;

R$_9$ is C$_1$-C$_4$alkyl;

R$_{10}$ is hydrogen or C$_1$-C$_4$alkyl;

X and Z independently of one another are hydrogen, C$_1$-C$_4$alkyl, C$_1$-C$_4$haloalkyl, phenylthio, benzylthio, hydroxy, halogen, —OR$_8$, —OR$_9$, C$_1$-C$_4$alkyl substituted by —OR$_9$, C$_1$-C$_4$-alkyl substituted by —OR$_8$, or —NH$_2$, —NHR$_9$, —NR$_9$(R$_9$), C$_3$-C$_6$cycloalkyl or C$_3$-C$_6$cycloalkyl substituted by halogen, $-OR_8$, $-OR_9$, $-SR_8$, $-SR_9$ or by $C_1-C_4$alkyl, with the proviso that at least one of the substituents X and Z is $C_3-C_6$cycloalkyl or $C_3-C_6$cycloalkyl substituted by halogen, $-OR_8$, $-OR_9$, $-SR_8$, $-SR_9$ or by $C_1-C_4$alkyl; and the salts of those compounds.

6. A compound of formula Ia according to claim 5, wherein $R_1$ is halogen, nitro, $C_1-C_4$alkyl, $C_1-C_4$haloalkyl, $-OR_8$, $-OR_9$, hydroxy, cyano or $-COOR_7$;

$R_5$ is hydrogen, halogen, nitro, $C_1-C_4$alkyl, $C_1-C_4$haloalkyl, $-OR_8$, $-OR_9$, hydroxy, cyano or $-COOR_7$; and X and Z independently of one another are hydrogen, $C_1-C_4$alkyl, $C_1-C_4$haloalkyl, $C_1-C_4$alkyl substituted by $-OR_9$, $C_1$-$C_4$alkyl substituted by $-OR_8$, or halogen $C_3-C_6$-cycloalkyl or $C_3-C_6$cycloalkyl substituted by halogen, $-OR_8$, $-OR_9$, $-SR_8$, $-SR_9$ or by $C_1-C_4$alkyl.

7. A compound of formula Ia according to claim 5, wherein $R_1$ is halogen, nitro, $C_1-C_2$alkyl, $C_1-C_2$haloalkyl, $-OR_8$, $-OR_9$, hydroxy, cyano or $-COOR_7$;

$R_5$ is hydrogen, halogen, nitro, $C_1-C_2$alkyl, $C_1-C_2$haloalkyl, $-OR_8$, $-OR_9$, hydroxy, cyano or $-COOR_7$;

$R_7$ is $C_1-C_2$alkyl, $C_2-C_3$alkenyl, $C_2-C_3$alkynyl, phenyl or benzyl;

$R_8$ is $C_1-C_2$haloalkyl;

$R_9$ is $C_1-C_2$alkyl; and

X and Z independently of one another are hydrogen, $C_1-C_2$alkyl, $C_1-C_2$haloalkyl, halogen, $C_3-C_6$cycloalkyl or $C_3-C_6$cycloalkyl substituted by halogen, $-OR_8$, $-OR_9$ or by $C_1-C_2$alkyl.

8. A compound of formula Ia according to claim 5, wherein $R_1$ is fluorine, chlorine, methyl, trifluoromethyl or methoxy;

$R_5$ is hydrogen, fluorine, chlorine, methyl, trifluoromethyl or methoxy; and

X and Z independently of one another are hydrogen, methyl, cyclopropyl, 1-methylcyclopropyl, 2-fluorocyclopropyl, 2,3-difluorocyclopropyl, 2-chlorocyclopropyl, 2,3-dichlorocyclopropyl, 2-methylcyclopropyl, 2,3-dimethylcyclopropyl, cyclopentyl, fluorine, chlorine or methoxy.

9. A compound of formula Ia according to claim 5, wherein $R_1$ is fluorine, chlorine, methyl or trifluoromethyl;

$R_5$ is hydrogen, chlorine, methyl or trifluoromethyl; and

X and Z independently of one another are hydrogen, cyclopropyl, 1-methylcyclopropyl, 2-fluorocyclopropyl, 2,3-difluorocyclopropyl, 2-chlorocyclopropyl, 2,3-dichlorocyclopropyl, 2-methylcyclopropyl, 2,3-dimethylcyclopropyl, methyl, methoxy, fluorine or chlorine.

10. A compound of formula Ia according to claim 9, wherein X is cyclopropyl.

11. A compound of formula I according to claim 1, wherein X is $C_3-C_6$cycloalkyl or $C_3-C_6$cycloalkyl substituted by halogen, $-OR_8$, $-OR_9$, $-SR_8$, $-SR_9$ or by $C_1-C_4$alkyl.

12. A compound of formula I according to claim 1, wherein X is cyclopropyl, 1-methylcyclopropyl, 2-fluorocyclopropyl, 2,3-difluorocyclopropyl, 2-chlorocyclopropyl, 2,3-dichlorocyclopropyl, 2-methylcyclopropyl or 2,3-dimethylcyclopropyl.

13. A compound of formula I according to claim 1, wherein X is cyclopropyl.

14. 5-Methyl-7-cyclopropyl-N-(2,6-difluorophenyl)-1,2,4-triazolo[1,5-a]pyrimidine-2-sulfonamide according to claim 1.

15. A herbicidal composition, which comprises as active ingredient a herbicidally effective amount of at least one triazolylsulfonamide of formula I according to claim 1, together with a carrier or other adjuvant.

16. A composition according to claim 15, which contains from 0.1% to 95% of a compound of formula I according to claim 1.

17. A method of controlling undesired plant growth, which comprises applying to by plants or to the locus thereof an effective amount of a compound of formula I according to claim 1 or of a composition containing that compound.

18. A method according to claim 17, wherein an amount of from 0.001 to 5 kg of compound is applied per hectare.

19. A method according to claim 17 of selectively controlling weeds pre- or postemergence in crops of useful plants.

20. 7-Cyclopropyl-5-methyl-N-(2,6-dichlorophenyl)-1,2,4-triazolo[1,5-a]pyrimidine-2-sulfonamide according to claim 1.

* * * * *